United States Patent [19]

Yoneyoshi et al.

[11] Patent Number: 5,231,227

[45] Date of Patent: Jul. 27, 1993

[54] OPTICALLY ACTIVE HYDROXYBENZYLAMINE DERIVATIVE AND PROCESS FOR PRODUCING SAID COMPOUND

[75] Inventors: Yukio Yoneyoshi, Otsu; Gohfu Suzukmo, Ibaraki, both of Japan; Yoji Sakito, Montreal, Canada

[73] Assignee: Sumitomo Chemical Company, Limited, Osaka, Japan

[21] Appl. No.: 861,634

[22] Filed: Apr. 1, 1992

Related U.S. Application Data

[62] Division of Ser. No. 652,607, Feb. 8, 1991, Pat. No. 5,120,853, which is a division of Ser. No. 251,789, Oct. 3, 1988, Pat. No. 5,011,989.

[30] Foreign Application Priority Data

Oct. 9, 1987 [JP] Japan ................... 62-256017

[51] Int. Cl.$^5$ ................... C07C 213/00; C07C 215/46
[52] U.S. Cl. ................... 564/390; 564/389
[58] Field of Search ................... 564/389, 390

[56] References Cited

U.S. PATENT DOCUMENTS

| | | | |
|---|---|---|---|
| 4,000,197 | 12/1976 | Barfknecht et al. | 260/570.8 R |
| 4,749,809 | 6/1988 | Yoneyoshi et al. | 564/9 X |
| 4,760,149 | 7/1988 | Yoneyoshi et al. | 564/9 X |

FOREIGN PATENT DOCUMENTS 0105696 4/1984 European Pat. Off. .
0237305 9/1987 European Pat. Off. .
3209788 9/1983 Fed. Rep. of Germany .
2029830 3/1980 United Kingdom .

OTHER PUBLICATIONS

Anales de la Souedad Espanola de Fisica Y Quimica, vol. 19 (1921) pp. 259-264.
J. Chem. Soc., Perkin Trans. I, 1985, 2039-2044, Itsuno et al., "Asymmetric Synthesis Using Chirally Modified Boronhydrides. Part 3 . . . ".
J. Org. Chem., vol. 37, No. 14, 1972, pp. 2347-2349, Borch et al., "An Asymmetric Synthesis of Alcohols, Amines, and Amino Acids".
Tetrhedron Letters, vol. 29, No. 2, pp. 223-224 1988, Sakito et al., "Asymmetric Reduction of Oxime Ethers, Distinction of Anti and Syn Isomers."
J. Chem. Soc., vol. 99, 1911, pp. 416-421, Moore, "Alpha-p-Hydroxy-m-methoxyphenylethylamine and the Resolution of . . . ".

Primary Examiner—Richard L. Raymond
Attorney, Agent, or Firm—Stevens, Davis, Miller & Mosher

[57] ABSTRACT

The optically active benzylamine derivatives of the present invention are very useful for use as the asymmetric ligand of an asymmetric reducing agent. By using the optically active amine-boron complex prepared from the compound of the present invention, optically active products can be obtained in a specifically high optical yield. Moreover, the separation and recovery of the reaction products and asymmetric ligand can be easily achieved.

12 Claims, No Drawings

OPTICALLY ACTIVE HYDROXYBENZYLAMINE DERIVATIVE AND PROCESS FOR PRODUCING SAID COMPOUND

This is a division of application Ser. No. 07/652,607, filed Feb. 8, 1991, now U.S. Pat. No. 5,120,853, which in turn is a division of application Ser. No. 07/251,789, filed Oct. 3, 1988, now U.S. Pat. No. 5,011,989.

The present invention relates to a novel optically active hydroxybenzylamine derivative represented by the formula (I)

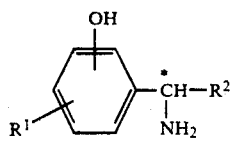

wherein $R^1$ denotes a hydrogen atom, lower alkyl group or lower alkoxy group; $R^2$ denotes a lower alkyl group; * signifies an asymmetric carbon atom; and the hydroxyl group is located on the phenyl at the ortho- or meta-position relative to the substituent having the asymmetric carbon, an optically active amine-boron compound having said derivative as a ligand, and a process for producing an optically active compound by using said compound.

Optically active benzylamine derivatives so far known include α-phenethylamine, and α-p-hydroxyphenylethylamine wherein the hydroxyl group is located at the para-position on the phenyl. It is also known that the former can be used as an asymmetric ligand for asymmetric reduction and the latter can be used as a resolving agent (see, for example, J. Chem. Soc., Perkin Trans., I, 371 (1978); J. Chem. Soc., 99, 416 (1911)).

However, nothing has yet been known about an optically active hydroxybenzylamine derivative represented by the formula (I) shown above wherein the hydroxyl group is located at the ortho- or meta-position on the phenyl group.

Further, the use of the above-mentioned optically active α-phenethylamine as the asymmetric ligand of asymmetric reducing agent accompanies such disadvantages that the optical yield of optically active compounds obtained by reduction is low, or the reduction products cannot be easily separated from the ligand.

The present inventors have synthesized various optically active benzylamine derivatives and, after extensive studies thereon, found that an optically active benzylamine derivative wherein the hydroxyl group is located at a specific position, namely ortho-or meta-position, on the phenyl group, when used as an asymmetric ligand of asymmetric reducing agent, gives a reduction product in a very high optical yield and yet can be separated from the reaction product very easily. The present invention has been accomplished on the basis of the above finding and additional extensive studies.

Thus, according to the present invention, there are provided a novel optically active hydroxybenzylamine derivative represented by the formula (I)

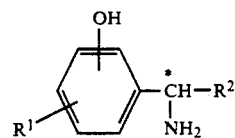

wherein $R^1$ denotes a hydrogen atom, lower alkyl group or lower alkoxy group; $R^2$ denotes a lower alkyl group; * signifies an asymmetric carbon atom; and the hydroxyl group is located on the phenyl at the ortho- or meta-position relative to the substituent having the asymmetric carbon atom, an optically active amine-boron compound having said derivative as a ligand, and a process for producing an optically active compound by using said compound.

The optically active hydroxybenzylamine derivative of the present invention is represented by the above formula (I). Preferably, the hydroxyl group is located at the ortho-position relative to the substituent having the asymmetric carbon atom.

Specific examples of the groups denoted by $R^1$ include hydrogen; lower alkyl groups such as methyl, ethyl, n-propyl, isopropyl, n-butyl, isobutyl, sec-butyl, t-butyl, pentyl and hexyl; and lower alkoxy groups such as methoxy, ethoxy, n-propoxy, isopropoxy, n-butoxy, isobutoxy, sec-butoxy, n-pentyloxy and n-hexyloxy. Specific examples of the groups denoted by $R^2$ include the same lower alkyl groups as those mentioned for $R^1$.

Specific examples of the compounds of the present invention, there may be mentioned optically active 1-(2-hydroxy-3-ethylphenyl)ethylamine, 1-(2-hydroxy-3-methylphenyl)ethylamine, 1-(2-hydroxy-3-methoxyphenyl)ethylamine, 1-(2-hydroxy-3-ethoxyphenyl)ethylamine, 1-(2-hydroxy-5-methoxyphenyl)ethylamine, 1-(2-hydroxyphenyl)ethylamine, 1-(2-hydroxy-5-ethoxyphenyl)ethylamine, 1-(2-hydroxyphenyl)propylamine, 1-(3-hydroxyphenyl)ethylamine, 1-(2-hydroxy-3-ethylphenyl)propylamine, 1-(2-hydroxy-3-methylphenyl)propylamine, 1-(2-hydroxy-3-methylphenyl)propylamine, 1-(2-hydroxy-3-ethylphenyl)propylamine, 1-(2-hydroxy-3-methoxyphenyl)propylamine, 1-(2-hydroxy-3-ethoxyphenyl)propylamine, 1-(2-hydroxy-5-methylphenyl)ethylamine, 1-(2-hydroxy-5-ethylphenyl)ethylamine, 1-(2-hydroxy-5-methoxyphenyl)propylamine, 1-(2-hydroxy-5-ethoxyphenyl)propylamine, 1-(2-hydroxy-4-methylphenyl)ethylamine, 1-(2-hydroxy-4-methoxyphenyl)ethylamine, 1-(2-hydroxy-4-methylphenyl)propylamine, 1-(2-hydroxy-4-methoxyphenyl)propylamine, 1-(3-hydroxyphenyl)propylamine, 1-(2-hydroxy-6-methylphenyl)ethylamine, 1-(2-hydroxy-6-methoxyphenyl)ethylamine, 1-(2-hydroxy-6-methylphenyl)propylamine, and 1-(2-hydroxy-6-methoxyphenyl)propylamine.

Such optically active benzylamine derivatives (I) may be prepared, for example, through the following route.

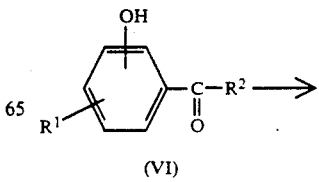

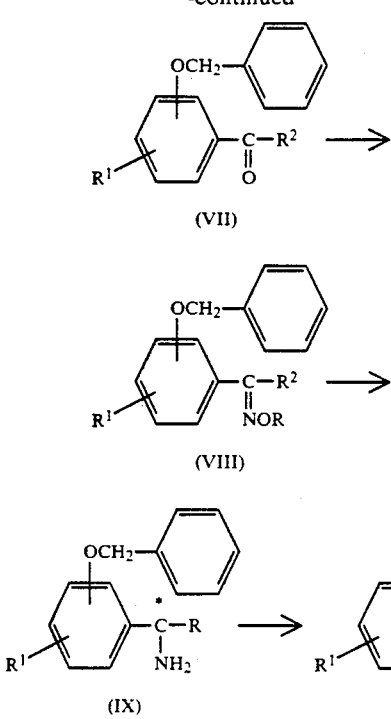

(VII)

(VIII)

(IX)   (I)

In a more specific example, a ketone compound of the formula (VI) and a benzyl halide are converted into a benzyl compound of the formula (VII) by Williamson synthesis, which is then allowed to react with hydroxylamine or alkoxylamines in such a solvent as pyridine to form an oxime compound of the formula (VIII), and then subjected to asymmetric reduction to prepare an optically active amine of the formula (IX). The above asymmetric reduction may be conducted, for example, with reference to the method described in J. Chem. Soc., Perkin Trans., I, 2039 (1985). For example, the compounds of the formula (I) can also be used as an asymmetric ligand.

The optically active amines of the formula (IX) may also be obtained by catalytically hydrogenating the oxime compound of the formula (VIII) with the aid of a hydrogenation catalyst such as palladium, platinum or Raney nickel, or by reducing said oxime compound with a metal hydride such as lithium aluminum hydride, sodium borohydride, borane.tetrahydrofuran complex and borane.dimethyl sulfide complex, to obtain a racemic amine of the formula (IX), followed by subjecting the amine to optical resolution.

The optically active benzylamine derivative of the formula (I) may then be obtained by subjecting the optically active amine of the formula (IX) to hydrogenolysis.

The hydrogenolysis can be accomplished by using conventional methods. For example, it is conducted in the presence of a catalyst such as palladium, platinum or Raney nickel.

The optically active amines (IX) may be used also in the form of their acids with mineral acids such as hydrochloric acid and sulfuric acid or organic acids such as acetic acid and propionic acid.

Though the solvent to be used is not particularly restricted so long as it does not poison the catalyst, usually alcohols such as methanol, ethanol and isopropanol or solvent mixtures thereof with water are used.

When catalysts other than Raney nickel are used, the reaction may also be conducted in the presence of mineral acids such as hydrochloric acid and sulfuric acid or organic acids such as acetic acid and propionic acid.

Although the reaction is usually carried out at $-50°$ to $+60°$ C. and at 0 to 150 kg/cm$^2$, it may be satisfactorily conducted at room temperature and at normal pressure.

Hereunder, the process for producing the amine-boron compound of the present invention having the optically active benzylamine derivative (I) as a ligand, and the process for producing optically active compounds by using the compound will be described.

The amine-boron compound of the present invention may be prepared, for example, from the derivative (I) and a boron hydride compound such as diborane, borane.tetrahydrofuran complex and borane.dimethyl sulfide complex. The molar ratio of the boron hydride compound to the number of moles of boron contained in the derivative (I) is normally 1 to 5, preferably 2 to 3.

There is no particular restriction as to the solvent so long as the solvent does not participate in the reaction. Specific examples of the solvents include ethers or thioethers such as diethyl ether, tetrahydrofuran, diglyme, and dimethyl sulfide; aromatic hydrocarbons such as benzene, toluene, xylene and chlorobenzene; halogenated hydrocarbons such as methylene chloride, 1,2-dichloroethane, chloroform, and carbon tetrachloride; and the solvent mixtures thereof.

The preparation is usually carried out at a temperature of $-78°$ to $+100°$ C., preferably $-40°$ to $+50°$ C. and normally in an atmosphere of inert gas such as nitrogen and argon.

Thus, the amine-boron compound of the present invention which has the derivative (I) as a ligand is prepared. The compound is highly fitted for use as an asymmetric reducing agent. For example, when asymmetric ketoximes or asymmetric ketones are reacted therewith, optically active amines are obtained from the former and optically active alcohols are obtained from the latter, respectively, in a high optical yield. Moreover, the separation of the reduction product from the ligand can be accomplished in simple operations of pH adjustment and liquid layer separation.

Firstly, the asymmetric reduction of prochiral ketoximes will be described. As an example, optically active amines represented by the formula (IV) can be prepared from the anti-form or syn-form isomer of oximes represented by the formula (II) or mixtures rich in either one of the isomers.

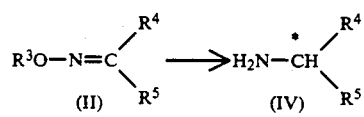

(II)   (IV)

wherein R$^3$ denotes a hydrogen atom, alkyl group, aralkyl group or alkyl-substituted silyl group; R$^4$ and R$^5$ are different from each other and each denotes a lower alkyl group, aryl group or aralkyl group; and * signifies an asymmetric carbon atom.

As examples of the substituent R$^3$ in oximes (II), there may be mentioned alkyl groups of 1 to 10 carbon atoms such as methyl, ethyl, propyl, butyl, pentyl, cyclopentyl, hexyl, cyclohexyl, heptyl, cycloheptyl, octyl, cyclooctyl, nonyl, and decyl; aralkyl groups of 7 to 11 carbon atoms such as benzyl, β-phenethyl and naphthylmethyl; and alkylsilyl groups of 3 to 12 carbon atoms such as trimethylsilyl, dimethyl-t-butylsilyl, tri-n-propylsilyl and tri-n-butylsilyl.

As examples of the substituents $R^4$ and $R^5$, there may be mentioned aryl groups of 5 to 17 total carbon atoms including phenyl, 2-, 3- and 4-pyridyl; halogen-substituted phenyls such as o-, m- and p-chlorophenyl, o-, m- and p-bromophenyl and 2,3-, 2,4-, 2,5-, and 2,6-dichlorophenyl; phenyls substituted with $C_1$-$C_6$ alkyls such as o-, m- and p-methylphenyl, o-, m- and p-ethylphenyl, o-, m- and p-butylphenyl and 2,3-, 2,4-, 2,5- and 2,6-dimethylphenyl; phenyls substituted with $C_1$-$C_6$ alkoxyls such as o-, m- and p-methoxyphenyl, o-, m- and p-ethoxyphenyl, and o-, m- and p-propoxyphenyl; benzyloxy-substituted phenyls such as o-, m- and p-benzyloxyphenyl, 2-benzyloxy-3-methylphenyl, 2-benzyloxy-4-methylphenyl, 2-benzyloxy-5-methylphenyl, 2-benzyloxy-5-t-butylphenyl, 2-benzyloxy-3-methoxyphenyl, 2-benzyloxy-4-methoxyphenyl, 2-benzyloxy-5-methoxyphenyl, and 2-benzyloxy-3,5-dichlorophenyl; and $\alpha$- and $\beta$-naphthyl; lower alkyl groups of 1 to 6 carbon atoms such as methyl, ethyl, propyl, butyl, pentyl, cyclopentyl, hexyl and cyclohexyl; and aralkyl groups of 7 to 11 carbon atoms such as benzyl, o-, m- and p-tolylmethyl, (o-, m- and p-ethylphenyl)methyl, (2,3-, 2,4-, 2,5- and 2,6-dimethylphenyl)methyl, 2-phenylethyl, 2-(o-, m- and p-tolyl)ethyl, (2,3-, 2,4-, 2,5- and 2,6-dimethylphenyl)ethyl, 3-phenylpropyl and naphthylmethyl.

Typical examples of ketoximes include O-methyl-, O-octyl-, O-cyclohexyl-, O-benzyl-, and O-trimethylsilyl-oximes or like oximes of acetophenone, propiophenone, butyrophenone, isobutyrophenone, 2-acetylpyridine, o-methoxyacetophenone, o-ethoxyacetophenone, o-propoxyacetophenone, o-benzyloxyacetophenone, $\alpha$-acetonaphthone, $\beta$-acetonaphthone, phenyl benzyl ketone, phenyl p-tolylmethyl ketone, phenyl m-tolylmethyl ketone, phenyl o-tolylmethyl ketone, phenyl 2-phenylethyl ketone, 2-butanone, 2-pentanone, 2-hexanone, 3-hexanone, 2-heptanone, 2-octanone, 3-heptanone, 3-octanone, cyclohexyl methyl ketone, cyclohexyl ethyl ketone, cyclohexyl benzyl ketone, $\alpha$-phenylacetone, 2-phenylethyl methyl ketone, 2-phenylethyl ethyl ketone, 3-phenylpropyl methyl ketone and the like. The syn-form or anti-form isomer of these oximes or mixtures thereof rich in either one of the isomers are used.

These ketoximes may be easily prepared from the corresponding ketones by well-known methods. When only one of the syn-form and anti-form isomers is used, the other isomer remaining after separation can be converted to the required isomer by syn/anti isomerization in a conventional manner, whereby effective utilization of the raw material can be achieved.

In the asymmetric reduction of prochiral ketoximes, the reducing agent is applied to the ketoximes in an amount of at least equivalent moles, usually 1 to 6 times by mole, as calculated in terms of the derivative (I). One to three times by mole is usually satisfactory for the purpose.

Solvents used in the reduction is not specifically restricted so long as they are inert ones which do not participate in the reduction. Examples of such solvents include aromatic hydrocarbons such as benzene, toluene, xylene and chlorobenzene; halogenated hydrocarbons such as methylene chloride, 1,2-dichloroethane, chloroform, and carbon tetrachloride; ether such as diethyl ether, tetrahydrofuran, dioxane, and diglyme; and solvent mixtures thereof. The amount of the solvent used is generally 2 to 50 times by weight based on the ketoximes.

The solvent which has been used in the step of preparing the reducing agent may be used as such, or after replenished with above-stated solvent, as the solvent for the reduction step.

The reduction in normally carried out in an inert gas atmosphere similar to that stated before. The reaction temperature is usually $-30°$ to $+100°$ C. and, in commercial production, generally $-10°$ to $+50°$ C.

After completion of the reduction, in general, an aqueous solution of a mineral acid such as hydrochloric acid is added to the reaction liquid to decompose the reducing agent. The resulting liquid is then made alkaline with an aqueous alkali solution such as aqueous caustic soda solution and separated into layers. The optically active amines, the intended reduction products, are recovered from the organic layer. On the other hand, the aqueous layer is neutralized with a mineral acid such as hydrochloric acid, or once acidified and then neutralized with an aqueous solution of an alkali such as ammonia, sodium hydrogen carbonate or sodium carbonate, and thereafter extracted with an organic solvent, whereby the optically active benzylamine derivative (I), the ligand, can be recovered in good yield without undergoing racemization, which may be reused as desired.

Then, the asymmetric reduction of prochiral ketones will be described below. As an example, optically active alcohols represented by the formula (V) can be prepared from ketones represented by the formula (III).

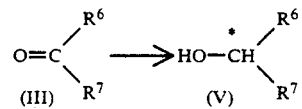

wherein $R^6$ and $R^7$ are different from each other and each denotes a lower alkyl group, aryl group, aralkyl group, or 2-substituted 1-triazolylethylene group represented by the formula (VI)

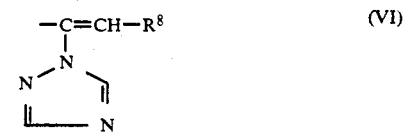

wherein $R^8$ denotes a cyclohexyl group, or a phenyl group which may be substituted with a halogen or haloalkyl group; and * signifies an asymmetric carbon atom.

Examples of the substituents $R^6$ and $R^7$ include the same lower alkyl groups, aryl groups and aralkyl groups as mentioned for $R^4$ and $R^5$ in the formulas (II) and (III), and 2-substituted 1-triazolylethylene group having, as the substituent $R^8$, phenyl, chlorophenyl, bromophenyl, dichlorophenyl, dibromophenyl, trifluoromethylphenyl, trichloromethylphenyl, tribromomethylphenyl, cyclohexyl, and the like.

As examples of typical ketones, there may be mentioned acetophenone, propiophenone, butyrophenone, isobutyrophenone, $\alpha$-acetonaphthone, $\beta$-acetonaphthone, phenyl benzyl ketone, phenyl p-tolylmethyl ketone, phenyl m-tolylmethyl ketone, phenyl o-tolylmethyl ketone, 2-butanone, 2-pentanone, 2-hexanone, 3-hexanone, 2-heptanone, 2-octanone, 1-phenyl-2-

(1,2,4-triazol-1-yl)-4,4-dimethyl-1-penten-3-one, 1-(4-chlorophenyl)-2-(1,2,4-triazol-1-yl)-4,4-dimethyl-1-penten-3-one, 1-(2,4-dichlorophenyl)-2-(1,2,4-triazol-1-yl)-4,4-dimethyl-1-penten-3-one, 1-cyclohexyl-2-(1,2,4-triazol-1-yl)-4,4-dimethyl-1-penten-3-one, 1-(4-trifluoromethylphenyl)-2-(1,2,4-triazol-1-yl)-4,4-dimethyl-1-penten-3-one, 1-(3-bromophenyl)-2-(1,2,4-triazol-1-yl)-4,4-dimethyl-1-penten-3-one and 1-(4-fluorophenyl)-2-(1,2,4-triazol-1-yl)-4,4-dimethyl-1-penten-3-one.

In the asymmetric reduction of ketones, the reducing agent is applied to the ketones in an amount of at least 0.5 time by mole, usually 0.5 to 6 times by mole, as calculated in terms of the derivative (I). Usually 1 to 3 times by mole is satisfactory for the purpose.

Solvents used in the reduction are not specifically restricted so long as they are inert ones which do not participate in the reduction. Examples thereof include aromatic hydrocarbons such as benzene, toluene, xylene and chlorobenzene; halogenated hydrocarbons such as methylene chloride, 1,2-dichloroethane, chloroform and carbon tetrachloride; esters such as diethyl ether, tetrahydrofuran, dioxane and diglyme; and the solvent mixtures thereof. The solvent which has been used in the step of preparing the reducing agent may be used as such, or after replenished with the above-stated solvent, as the solvent for the reduction step. The amount of the solvent used is in general 2 to 50 times by weight based on the ketones.

The reduction is normally carried out in an inert gas atmosphere similar to that stated before. The reaction temperature is usually $-30°$ to $+100°$ C. and, in commercial production, generally $-10°$ to $+50°$ C.

After completion of the reduction, in general, an aqueous solution of a mineral acid such as hydrochloric acid is added to the reaction liquid to decompose the reducing agent. The resulting liquid is then separated into layers under acid conditions. The optically active alcohols, the intended reduction products, are recovered from the organic layer. On the other hand, the aqueous layer is neutralized with an aqueous solution of alkali such as ammonia, sodium hydrogen carbonate or sodium carbonate and then extracted with an organic solvent, whereby the optically active benzylamine derivative (I) of the ligand can be recovered in good yield without undergoing racemization, which may be reused as desired.

The optically active benzylamine derivatives of the present invention are very useful for use as the asymmetric ligand of an asymmetric reducing agent. By using the optically active amine-boron complex prepared from the compound of the present invention, optically active reduction products can be obtained in a specifically high optical yield and moreover the separation and recovery of the reaction products and asymmetric ligand can be accomplished very easily.

The present invention will be described in detail below with reference to the following examples, but it is not limited to these examples.

REFERENTIAL EXAMPLE 1

Preparation of Benzyl Compound

A sodium ethylate solution was prepared from 200 ml of ethanol and 7.9 g (0.3435 g-atom) of metallic sodium. Then 0.312 mole (42.52 g) of 2-hydroxyacetophenone and 47.47 g (0.375 mole) of benzyl chloride were added thereto, and the resulting mixture was stirred under reflux for 4 hours.

The reaction mixture was then cooled down to room temperature and the sodium chloride formed was filtered off. The filtrate was concentrated under reduced pressure and extracted with toluene. The toluene extract was washed with water, dried and then distilled under reduced pressure to obtain 66.06 g of 2-benzyloxyacetophenone.

In place of 2-hydroxyacetophenone, there were used 2-hydroxypropiophenone, 2-hydroxy-3-methylacetophenone, 2-hydroxy-3-methoxyacetophenone, 2-hydroxy-5-methoxyacetophenone and 3-hydroxyacetophenone to obtain the corresponding benzyl compounds.

TABLE 1

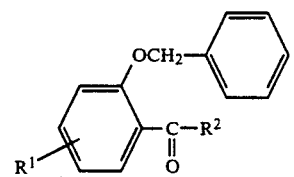

| No. | $R^1$ | $R^2$ | Yield (%) | B.p. (°C./mmHg) |
|---|---|---|---|---|
| 1 | H | $CH_3$ | 94 | 140–142/0.3 |
| 2 | H | $C_2H_5$ | 90 | 140–144/0.2 |
| 3 | 3-$CH_3$ | $CH_3$ | 80 | 127–132/0.3 |
| 4 | 3-$OCH_3$ | $CH_3$ | 56 | 160–161/0.6 |
| 5 | 5-$OCH_3$ | $CH_3$ | 75 | 162–163/0.3 |
| 6 | 3-Benzyloxyacetophenone | | 91 | 155/0.3 |

REFERENCIAL EXAMPLE 2

Preparation of Oxime Compound

To 50 ml of pyridine were added 0.0434 mole (9.77 g) of 2-benzyloxyacetophenone prepared in the first and second paragraphs in Referential Example 1 (Table 1, No. 1) and 4.35 g (0.0521 mole) of O-methylhydroxylamine hydrochloride. The mixture was stirred at room temperature for 2 hours and then at 100° C. for 1 hour. The reaction liquid was cooled down to room temperature, 300 ml of water was added thereto, and the oil layer was separated off. The aqueous layer was extracted with chloroform and the extract was combined with said oil layer, washed with water, dried and distilled under reduced pressure to obtain 10.77 g of 2-benzyloxyacetophenone O-methyloxime.

In the same manner but by using the benzyl compounds shown in the third paragraph in Referential Example 1 (Table 1, Nos. 2–6), the corresponding oxime compounds were obtained.

TABLE 2

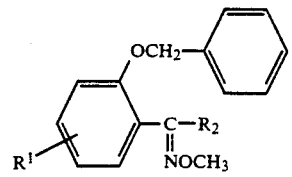

| No. | $R^1$ | $R_2$ | Anti/Syn | B.p. (°C./mmHg) | Yield (%) |
|---|---|---|---|---|---|
| 1 | H | $CH_3$ | 88/12 | 135–141/0.2 | 97 |
| 2 | H | $C_2H_5$ | 80/20 | 133–140/0.2 | 94 |
| 3 | 3-$CH_3$ | $CH_3$ | 87/13 | 127–132/0.3 | 97 |
| 4 | 3-$OCH_3$ | $CH_3$ | 88/12 | 150–154/0.4 | 97 |

TABLE 2-continued

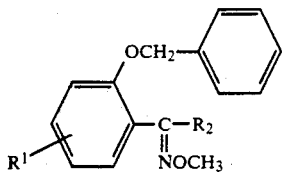

| No. | R$^1$ | R$^2$ | Oxime Anti/Syn | B.p. (°C./mmHg) | Yield (%) |
|---|---|---|---|---|---|
| 5 | 5-OCH$_3$ | CH$_3$ | 86/14 | 155-158/0.3 | 97 |
| 6 | 3-Benzyloxy-acetophenone O-methyloxime | | 96/4 | 147/0.2 | 95 |

REFERENTIAL EXAMPLE 3

Preparation of Optically Active α-(Benzyloxyphenyl)alkylamine (3-1) (+)-1-(2-Benzyloxyphenyl)ethylamine A mixture of 200 ml of tetrahydrofuran (THF) and 13.79 g (0.054 mole) of (S)-(−)-2-amino-3-methyl-1,1-diphenylbutanol was cooled to −78° C. Then 4.31 g of borane.dimethyl sulfide complex was added thereto with stirring, and the temperature of the mixture was raised to room temperature over a period of about 2 hours. Then, 4.31 g of borane.dimethyl sulfide complex was further added to the mixture, which was then stirred for 15 minutes.

Then, a mixture of 9.19 g (0.036 mole) of 2-benzyloxyacetophenone O-methyloxime obtained in the first paragraph in Referential Example 2 (Table 2, No. 1) and 10 ml of THF was added thereto and the resulting mixture was stirred at room temperature for 20 hours and then at 60° C. for 1 hour.

Then, 70 ml of 10% hydrochloric acid was added to the mixture and stirred at 50° C. for 1.5 hours. The reaction liquid was concentrated under reduced pressure, made alkaline by addition of 10% aqueous sodium hydroxide solution, and extracted twice with chloroform. The organic layer was washed with water, dried, concentrated, and subjected to silica gel column chromatography with ethyl acetate as the eluting solvent, to separate and remove the ligand. Thus, 6.08 g of (+)-1-(2-benzyloxyphenyl)ethylamine was obtained.

$^1$H-NMR spectrum [δ ppm, CDCl$_3$] 1.41 (3H, d), 2.16 (2H, s), 4.43 (1H, q), 5.08 (2H, s), 6.89–7.00 (2H, m), 7.12–7.23 (1H, m), 7.28–7.44 (7H, m)

The hydrochloride of the above amine showed an optical rotation [α]$_D^{20}$ of +13.45° (C 1.05, water).

The hydrochloride was recrystallized from isopropanol to obtain 4.64 g of crystals having an [α]$_D^{20}$ of +16.44° (C 1.09, water). A part thereof was reacted with 3,5-dinitrophenyl isocyanate to be converted into its urea derivative, which was then analyzed by high performance liquid chromatography with an optically active column. It was found that the optical purity was 87.2%.

(3-2) (+)-1-(2-Benzyloxyphenyl)propylamine

A mixture of 140 ml of THF and 9.30 g (0.0364 mole) of (S)-(−)-2-amino-3-methyl-1,1-diphenylbutanol was cooled to −78° C. and 2.90 g of borane.dimethyl sulfide complex was added thereto with stirring. The temperature of the mixture was then raised to room temperature over a period of about 3 hours. Then, 2.90 g of borane.dimethyl sulfide complex was further added to the mixture, which was then stirred for 15 minutes.

Then, a mixture of 7 g (0.026 mole) of 2-benzyloxypropiophenone O-methyloxime obtained in the second paragraph in Referential Example 2 (Table 2, No. 2) and 10 ml of THF was added, and the resulting mixture was stirred at room temperature for 20 hours and then at 50° C. for 1 hour.

Then, the reaction liquid was treated according to the same procedures as in Referential Example (3-1) involving addition of 10% hydrochloric acid, concentration under reduced pressure, neutralization with alkali, extraction with chloroform and purification by column chromatography, to obtain 4.5 g of (+)-1-(2-benzyloxyphenyl)propylamine; which had an oily appearance and an optical purity of 49.6%.

$^1$H-NMR spectrum [δ ppm, CDCl$_3$] 0.89 (3H, t), 1.58 (2H, s), 1.67–1.98 (2H, q), 4.12 (H, t), 5.08 (2H, s), 6.8–7.35 (4H, m), 7.39 (5H, s).

In 170 ml of water was dissolved 5.17 g of the hydrochloride of the above amine, and a solution consisting of 3.23 g of N-acetyl-L-leucine and 18.6 ml of 1N NaOH solution was added. Collecting the precipitated crystals by filtration gave 3.40 g of N-acetyl-L-leucine salt of (+)-1-(2-benzyloxyphenyl)propylamine, having an [α]$_D^{20}$ of +12.1° (C 0.5, water).

Then, the salt obtained above was added to aqueous sodium hydroxide solution to form free amine, which was then extracted with chloroform to obtain 1.95 g of (+)-1-(2-benzyloxyphenyl)propylamine as an oil, having an optical purity of 97.0% and an [α]$_D^{20}$ of +14.86° (C 1.0, water) (hydrochloride).

(3-3) (−)-1-(2-Benzyloxy-3-methylphenyl)ethylamine

A mixture of 15.83 g (0.062 mole) of (S)-2-amino-3-methyl-1,1-diphenylbutanol and 260 ml of 1,2-dichloroethane was cooled to −30° C., 4.95 g of borane.dimethyl sulfide complex was added thereto, and the temperature of the mixture was elevated to 10° C. over a period of 2 hours. Then, 4.95 g of borane.dimethyl sulfide complex was further added thereto, and the temperature was raised to room temperature over a period of 1 hour.

Then, a mixture of 11.93 g (0.0443 mole) of 2-benzyloxy-3-methylacetophenone O-methyloxime obtained in the second paragraph in Referential Example 2 (Table 2, No. 3) and 15 ml of 1,2-dichloroethane was added, the resulting mixture was stirred at room temperature for 21 hours and then at 50° C. for 1 hour, and then 120 ml of 10% hydrochloric acid was added thereto.

The thus precipitated (S)-(−)-2-amino-3-methyl-1,1-diphenylbutanol hydrochloride was filtered off. The filtrate was made alkaline with aqueous sodium hydroxide solution, and the organic layer was separated and concentrated under reduced pressure.

The concentrate was then purified by silica gel column chromatography with ethyl acetate used as eluting solvent to remove the ligand and other impurities contained in a small amount. Thus, 5.2 g of (−)-1-(2-benzyloxy-3-methylphenyl)ethylamine was obtained, having an [α]$_D^{20}$ of −4.8° (C 1.4, methanol) and an optical purity of 79.8%.

$^1$H-NMR spectrum [δ ppm, CDCl$_3$] 1.36 (3H, d), 1.62 (2H, s), 2.35 (3H, s), 4.47 (H, q), 4.85 (2H, s), 7.0–7.6 (8H, m).

(3-4) (−)-1-(2-Benzyloxy-3-methoxyphenyl)ethylamine

Reactions and purifications were carried out in the same manner as in Referential Example (3-3) except that 8.56 g (0.03 mole) of 2-benzyloxy-3-methoxyacetophenone O-methyloxime obtained in Referential Example 2 (Table 2, No. 4) was used as the oxime ether compound, to obtain 5.0 g of (−)-1-(2-benzyloxy-3-methoxyphenyl)ethylamine having an optical purity of 73.6% and an $[\alpha]_D^{20}$ of −28.1° (C 1.0, water) (hydrochloride).

The hydrochloride of the above amine was dissolved in 20 ml of water and added to a solution consisting of 3.36 g of N-acetyl-L-leucine and 19.1 ml of aqueous 1N sodium hydroxide solution.

The precipitated crystals were collected by filtration, converted to free amine by use of aqueous sodium hydroxide solution and then extracted with methylene chloride. Thus, 3.17 g of (−)-1-(2-benzyloxy-3-methoxyphenyl)ethylamine was obtained; which had an optical purity of 95.0% and an $[\alpha]_D^{24}$ of −35.66° (C 0.99, water) (hydrochloride).

$^1$H-NMR spectrum [δ ppm, CDCl$_3$] 1.29 (3H, d), 2.63 (2H, s), 3.88 (3H, s), 4.83 (1H, q), 5.04 (2H, s), 6.8–7.17 (3H, m), 7.2–7.55 (5H, m).

(3-5) (+)-1-(2-Benzyloxy-5-methoxyphenyl)ethylamine

Reactions and purifications were carried out in the same manner as in Referential Example (3-3) except that 7.42 g (0.026 mole) of 2-benzyloxy-5-methoxyacetophenone O-methyloxime obtained in Referential Example 2 (Table 2, No. 5) was used as the oxime ether compound. Thus, 3.76 g of (+)-1-(2-benzyloxy-5-methoxyphenyl)ethylamine was obtained. The hydrochloride thereof showed an optical rotation $[\alpha]_D^{26}$ of +2.45° (C 0.94, water). Recrystallization from isopropanol yielded 2.68 g of purified product having an optical purity of 95.2% and an $[\alpha]_D^{24}$ of +3.41° (C 1.0, water) (hydrochloride).

$^1$H-NMR spectrum [δppm, CDCl$_3$] 1.39 (3H, d), 1.69 (2H, s), 3.77 (3H, s), 4.42 (2H, q), 5.04 (2H, s), 6.6–7.0 (3H, m), 7.2–7.5 (5H, m).

(3-6) (−)-1-(3-Benzyloxyphenyl)ethylamine

Reactions and purifications were carried out in the same manner as in Referential Example (3-3) except that 6.64 g of 3-benzyloxyacetophenone O-methyloxime obtained in Referential Example (2-6) was used as the oxime ether compound, to obtain (−)-(3-benzyloxyphenyl)ethylamine; which had an optical purity of 87.4% and an $[\alpha]_D^{26}$ of −2.56° (C 1.05, water) (hydrochloride).

(3-7) (−) and (+)-1-(2-Benzyloxyphenyl)ethylamine

To a solution consisting of 56.26 g (0.22 mole) of 2-benzyloxyacetophenone O-methyloxime obtained in the same manner as in Referential Example 2 (Table 2, No. 1) and 250 ml of THF, was added 26.74 g (0.352 mole) of borane.dimethyl sulfide complex at room temperature. The resulting mixture was stirred for 5 hours and then allowed to stand overnight.

Then, 10% hydrochloric acid solution was added to the reaction mass to decompose the reducing agent. The reaction mixture was then made alkaline by addition of aqueous sodium hydroxide solution, extracted with methylene chloride, washed with water, dried, concentrated and distilled to obtain 48.6 g of (±)-1-(2-benzyloxyphenyl)ethylamine, having a b.p. 152°–153° C./18 mmHg.

The above amine was made into its hydrochloride with hydrochloric acid. To a solution consisting of 1.319 g (5 mmoles) of the hydrochloride and 14 ml of water, were added at room temperature 0.761 g (5 mmoles) of (+)-mandelic acid, 1 ml of water and 5 ml of aqueous 1N sodium hydroxide solution, whereby crystals were precipitated. After addition of 5 ml of water followed by recrystallization, 0.93 g of the (+)-mandelic acid salt ($[\alpha]_D^{24}$ +36.3° (C 0.97, water)) of crude (−)-1-(2-benzyloxyphenyl)ethylamine was obtained. It was then recrystallized from water to give 0.53 g of purified salt ($[\alpha]_D^{24}$ +32.04° (C 0.82, water)). The salt was decomposed with aqueous sodium hydroxide solution and extracted with chloroform to give 0.31 g of (−)-1-(2-benzyloxyphenyl)ethylamine ($[\alpha]_D^{24}$ −19.1° (C 1.0, water) (hydrochloride)). Analysis by high performance liquid chromatography with an optically active column showed an optical purity of 99% or more.

Crystals which had been precipitated from the mother liquor obtained after separation of said (+)-mandelic acid salt of crude (−)-1-(2-benzyloxyphenyl)ethylamine were collected by filtration and dried to give 0.31 g of (+)-mandelic acid salt of (+)-(2-benzyloxyphenyl)ethylamine; $[\alpha]_D^{25}$ 59.35° (C 0.83, water).

The above salt was decomposed with aqueous sodium hydroxide solution and extracted with chloroform to give 0.18 g of (+)-1-(2-benzyloxyphenyl)ethylamine ($[\alpha_D^{25}$ +19.27° (C 1.1, water) (hydrochloride)); optical purity: 98.2%, m.p.: 154°–156° C. (hydrochloride).

EXAMPLE 1

A mixture obtained by adding 2.64 g of (+)-1-(2-benzyloxyphenyl)ethylamine hydrochloride prepared in Referential Example (3-1) and 0.26 g of 5% Pd-C to 40 ml of methanol was subjected to hydrogenation at room temperature and normal pressure, whereby 256 ml of hydrogen was absorbed. After filtering off the catalyst, the filtrate was concentrated under reduced pressure to give 1.78 g of (+)-1-(2-hydroxyphenyl)ethylamine hydrochloride.

$[\alpha]_D^{17}$ +21.36° (C 1.06, water), m.p.: 135°–136° C.

The above salt was neutralized with aqueous ammonia solution and extracted with methylene chloride to give 1.30 g of (+)-1-(2-hydroxyphenyl)ethylamine.

$[\alpha]_D^{24}$ +12.24° (C 1.1, CHCl$_3$), m.p.: 83°–83.5° C.

NMR spectrum [δppm, CDCl$_3$-DMF-d$_7$] (hydrochloride) 1.70 (3H, d), 4.70 (1H, q), 6.6–7.5 (4, m), 7.4–8.7 (4H, broad)

EXAMPLE 2

In the same manner as in Example 1 except for using 1.37 g of (+)-1-(2-benzyloxyphenyl)propylamine hydrochloride obtained in Referential Example (3-2) in place of (+)-1-(2-benzyloxyphenyl)ethylamine used in Example 1, 0.95 g of (+)-1-(2-hydroxyphenyl)propylamine hydrochloride was obtained.

$[\alpha]_D^{21}$ +28.6° (C 1.2, water), m.p.: 194°–196° C.

The above salt was neutralized and treated in the same manner as in Example 1 to obtain 0.72 g of free amine as an oily substance.

$[\alpha]_D^{22}$ +17.21° (C 1.32, CHCl$_3$)

NMR spectrum [δppm, CDCl$_3$] 0.89 (3H, t), 3.96 (H, t), 1.75 (2H, m), 6.6–7.25 (4H, m), 3.5–5.5 (3H, broad)

EXAMPLE 3

Procedures involving reaction and neutralization were followed in the same manner as in Example 1 except for using (−)-1-(2-benzyloxy-3-methylphenyl)ethylamine hydrochloride obtained in Referential Example (3-3) in place of (+)-1-(2-benzyloxyphenyl)ethylamine used in Example 1, to obtain 1.38 g of (+)-1-(2-hydroxy-3-methylphenyl)ethylamine as crystals. Recrystallization from cyclohexane gave 1.08 g of a purified product of an optical purity of 98.8%.

$[\alpha]_D^{25}$ +17.8° (C 1.1, CHCl$_3$), m.p.: 115°-116° C

NMR spectrum [δppm, CDCl$_3$-DMF-d$_7$] (hydrochloride) 1.68 (3H, d), 4.80 (1H, q), 2.29 (3H, s), 6.68-7.40 (3H, m), 7.8-9.0 (4H, broad)

EXAMPLE 4

Procedures involving reaction and neutralization were followed in the same manner as in Example 1 except for using 3.21 g of (−)-1-(2-benzyloxy-3-methoxyphenyl)ethylamine hydrochloride obtained in Referential Example (3-4) in place of (+)-1-(2-benzyloxyphenyl)ethylamine used in Example 1, to obtain 1.81 g of crystals of (+)-1-(2-hydroxy-3-methoxyphenyl)ethylamine.

$[\alpha]_D^{24}$+13.14° (C 1.04, ethyl acetate), m.p.: 95°-97° C.

NMR spectrum [δ ppm, CDCl$_3$]1.46 (3H, d), 3.86 (3H, s), 4.35 (1H, q), 4.4-5.0 (3H, broad)

EXAMPLE 5

Procedures involving reaction and neutralization were followed in the same manner as in Example 1 except for using 2.57 g of (+)-1-(2-benzyloxy-5-methoxyphenyl)ethylamine hydrochloride obtained in Referential Example (3-6) in place of (+)-1-(2-benzyloxyphenyl)ethylamine used in Example 1, to obtain 1.42 g of (+)-1-(2-hydroxy-5-methoxyphenyl)ethylamine as an oily substance.

$[\alpha]_D^{22}$+21.70° (C 0.96, chloroform)

EXAMPLE 6

Reaction was carried out in the same manner as in Example 1 except for using 3.21 g of (−)-1-(3-benzyloxyphenyl)ethylamine hydrochloride obtained in Referential Example (3-6) in place of (+)-1-(2-benzyloxyphenyl)ethylamine hydrochloride used in Example 1.

After catalyst removal by filtration, concentration under reduced pressure, neutralization with ammonia and extraction with ethyl acetate, 1.60 g of (−)-1-(3-hydroxyphenyl)ethylamine was obtained.

$[\alpha]_D^{24}$ −24.52° (C 0.98, ethyl acetate)

NMR spectrum (δppm, CDCl$_3$) 1.40 (3H, d), 3.0-3.4 (3H, s), 4.09 (1H, q), 6.6-6.9 (3H, m), 7.08-7.2 (1H)

EXAMPLE 7

In a nitrogen atmosphere, 0.10 ml (1 mmole) of borane.dimethyl sulfide complex was added to a a solution consisting of 0.1372 g (1 mmole) of (+)-1-(2-hydroxyphenyl)ethylamine and 4 ml of deuterochloroform at 0° C., and the mixture was stirred at the temperature for 1 hour and then at room temperature for 0.5 hour.

Then, 0.10 ml (1 mmole) of borane.dimethyl sulfide complex was further added thereto and stirred at room temperature for 0.75 hour. Thus, an optically active amine-boron compound was prepared.

The $^{11}$B-NMR spectrum of the compound was determined as follows: [δ ppm, reference: BF$_3$.OEt$_2$]−37.1, −20.2, +1.3, +2.5, +21.0, +26.1

EXAMPLES 8 to 10

Optically active amine-boron compounds were prepared in the same manner as in Example 7 but by using (+)-1-(2-hydroxy-3-methoxyphenyl)ethylamine, (+)-1-(2-hydroxy-3-methylphenyl)ethylamine and (+)-1-(2-hydroxy-5-methoxyphenyl)ethylamine, respectively, in place of (+)-1-(2-hydroxyphenyl)ethylamine used in Example 7. The results of determination of $^{11}$B-NMR of the compounds obtained are shown in Table 1.

TABLE 1

| Example No. | $^{11}$B-NMR spectrum [δppm, reference: BF$_3$.OEt$_2$] |
|---|---|
| 8 | −39.0, −20.3, +1.0, +21.0, +27.2 |
| 9 | −20.4, −5.0, +0.5, +1.5, +20.8, +26.9 |
| 10 | −20.4, +1.3, +2.3, +20.8, +26.7 |

EXAMPLE 11

A mixture of 0.9 mmole (0.124 g) of (+)-1-(2-hydroxyphenyl)ethylamine obtained in Example 1 and 2.5 ml of THF was cooled to −78° C., 0.9 mmole (1.15 ml) of 0.78M borane.THF solution was added thereto, and the mixture was brought up to room temperature with stirring over a period of 2 hours. Then, 0.9 mmole of 0.78M borane.THF solution was further added thereto, followed by stirring for 30 minutes.

Then, at room temperature, a solution consisting of 0.6 mmole (0.153 g) of 2-benzyloxyacetophenone O-methyloxime (anti/syn=88/12) and 2 ml of THF was added thereto, and the resulting mixture was stirred at room temperature for 24 hours and then at 45° C. for 1.5 hours.

Then, 4 ml of 10% hydrochloric acid was added to the reaction mass, which was then concentrated under reduced pressure, mixed with diethyl ether and water, and separated into layers. The aqueous layer was made alkaline with aqueous sodium hydroxide solution and extracted with chloroform to obtain 0.12 g of (−)-1-(2-benzyloxyphenyl)ethylamine in 88% yield. The optical yield was 50%.

The aqueous layer which remained after said extraction with chloroform was acidified with hydrochloric acid, then neutralized with ammonia and extracted with chloroform, whereby 0.10 g of (+)-1-(2-hydroxyphenyl)ethylamine was recovered as crystals. The optical purity was found to be 87.2%, the same as that before use.

EXAMPLES 12 TO 18 AND COMPARATIVE EXAMPLE 1

According to the procedures of Example 11, a series of asymmetric reduction of acetophenone O-methyloxime (anti/syn=97/3) was carried out by using various optically active benzylamines obtained in Examples 1 to 6 and (−)-1-(4-hydroxyphenyl)ethylamine as the asymmetric ligand, to obtain (+)-α-phenethylamine. The results obtained are shown in Table 3.

TABLE 3

| | Asymmetric ligand*1) | | Boron hydride compound | Reaction solvent | Optical yield*2) (%) |
|---|---|---|---|---|---|
| | R$_1$ | R$_2$ | | | |
| Example | | | | | |
| 12 | H | CH$_3$ | BH$_3$.THF | THF | 66 |
| 13 | " | " | BH$_3$.S(CH$_3$)$_2$ | 1,2-Dichloroethane | 74 |
| 14 | " | C$_2$H$_5$ | " | 1,2-Dichloroethane | 71 |
| 15 | 3-CH$_3$ | CH$_3$ | " | 1,2-Dichloroethane | 78 |
| 16 | 3-OCH$_3$ | " | " | 1,2-Dichloroethane | 84 |
| 17 | 5-OCH$_3$ | " | " | 1,2- | 73 |

TABLE 3-continued

| | Asymmetric ligand*[1] | | Boron hydride compound | Reaction solvent | Optical yield*[2] (%) |
|---|---|---|---|---|---|
| | $R_1$ | $R_2$ | | | |
| 18 | (−)-1-(3-Hydroxy- phenyl)- ethylamine | | " | Dichloro- ethane THF | 26 |
| Comparative Example 1 | (−)-1-(4-Hydroxy- phenyl)- ethylamine | | " | " | 11 |

Note:

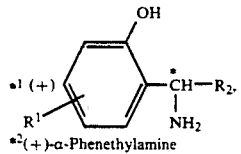

*[2] (+)-α-Phenethylamine

EXAMPLES 19 TO 29

Reactions were carried out in the same manner as in Example 11 except for using the various substrates shown in Table 4 in place of 2-benzyloxyacetophenone O-methyloxime used in Example 11. The results thus obtained are shown in Table 4.

EXAMPLE 30

Reaction was carried out in the same manner as in Example 11 except for using (−)-1-(3-hydroxyphenyl)ethylamine in place of (+)-1-(2-hydroxyphenyl)ethylamine and using phenyl p-tolylmethyl ketone O-methyloxime in place of 2-benzyloxyacetophenone O-methyloxime. The results obtained are shown in Table 4.

COMPARATIVE EXAMPLE 2

In the same manner as in Example 31 except for using (−)-1-(4-hydroxyphenyl)ethylamine was used in place of (−)-1-(3-hydroxyphenyl)ethylamine used in Example 30. The results obtained are shown in Table 4.

TABLE 4

| | Substrate | Boron hydride compound | Reaction solvent | Product | Optical yield (%) |
|---|---|---|---|---|---|
| Example | | | | | |
| 19 | 2-Methoxyacetophenone O-methyloxime (anti) | $BH_3 \cdot THF$ | THF | (−)-1-(2-Methoxyphenyl)- ethylamine | 67 |
| 20 | 2-Isopropoxyacetophenone O-methyloxime (anti/syn = 87/13) | " | " | (−)-1-(2-Isopropoxy- phenyl)ethylamine | 49 |
| 21 | 4-Bromoacetophenone O-methyloxime (anti/syn = 97/3) | $BH_3 \cdot SMe_2$ | " | (−)-1-(4-Bromophenyl)- ethylamine | 69 |
| 22 | 1-Acenaphthone O-methyloxime (syn) | " | 1,2-Dichloro- ethane | (31 )-1-(1-Naphthyl)- ethylamine | 67 |
| 23 | 1-Acenaphthone O-methyloxime (anti) | " | " | (+)-1-(1-Naphthyl)- ethylamine | 68 |
| 24 | 2-Octanone O-benzyloxime (anti) | " | 1,2-Dichloro- ethane | (−)-1-Methylheptylamine | 74 |
| 25 | Cyclohexyl benzyl ketone O-methyloxime (syn) | " | " | (−)-1-Cyclohexyl-2- phenylethylamine | 80 |
| 26 | Phenyl p-tolylmethyl ketone O-n-octyloxime (anti) | " | " | (+)-1-Phenyl-2-(p-tolyl)- ethylamine | 71 |
| 27 | Phenyl p-tolylmethyl ketone O-trimethyl- silyloxime (anti) | $BH_3 \cdot SMe_2$ | 1,2-Dichloro- ethane | (−)-1-Phenyl-2-(p-tolyl)- ethylamine | 69 |
| 28 | Phenyl p-tolylmethyl ketone O-methyloxime (syn) | " | " | (+)-1-Phenyl-2-(p-tolyl)- ethylamine | 76 |
| 29 | Phenyl-p-tolylmethyl ketone O-methyloxime (anti) | " | " | (−)-1-Phenyl-2-(p-tolyl)- ethylamine | 77 |
| 30 | Phenyl-p-tolylmethyl ketone O-methyloxime (anti) | " | THF | (−)-1-Phenyl-2-(p-tolyl)- ethylamine | 19 |
| Comparative Example 2 | Phenyl-p-tolylmethyl ketone O-methyloxime (anti) | " | " | (−)-1-Phenyl-2-(p-tolyl)- ethylamine | 1 |

EXAMPLE 31

In a nitrogen atmosphere, 3.75 mmole (0.375 ml) of borane.dimethyl sulfide complex was added at −30° C. to a solution consisting of 1.5 mmoles (0.206 g) of (+)-1-(2-hydroxyphenyl)ethylamine and 4 ml of THF, and the resulting mixture was brought up to room temperature over a period of 2 hours.

Then, a solution consisting of 1 mmole (0.12 g) of acetophenone and 1 ml of THF was added to the mixture and stirred for 24 hours.

Thereafter, 3 ml of 10% hydrochloric acid was added thereto, the resulting mixture was stirred at 50° C. for 1 hour and then extracted with chloroform. The extract was washed with 10% hydrochloric acid and then with water, and dried to obtain (−)-1-phenylethanol in 100% conversion.

The above product was converted into the urethane derivative and analyzed for its isomer ratio by high performance liquid chromatography with an optically active column and the optical yield was determined. The results obtained are shown in Table5.

EXAMPLES 32 TO 34

The procedures in Example 31 were repeated except that n-propyl phenyl ketone, isopropyl phenyl ketone and methyl n-hexyl ketone were used respectively in place of acetophenone used in Example 31. The results obtained are shown in Table 5.

EXAMPLE 35

The procedures in Example 31 were repeated except that (−)-1-(3-hydroxyphenyl)ethylamine was used in place of (+)-1-(2-hydroxyphenyl)ethylamine used in Example 31. The results obtained are shown in Table 5.

COMPARATIVE EXAMPLE 3

The procedures in Example 31 were repeated except that (+)-α-phenylethylamine was used in place of (+)-1-(2-hydroxyphenyl)ethylamine used in Example 31. The results obtained are shown in Table 5.

TABLE 5

| Example | Substrate | Product | Optical yield (%) |
|---|---|---|---|
| 31 | Acetophenone | (−)-1-Phenylethanol | 23 |
| 32 | n-Propyl phenyl ketone | (31)-1-Phenylbutanol | 24 |
| 33 | i-Propyl phenyl ketone | (−)-1-Phenyl-2-methylpropanol | 19 |
| 34 | Methyl n-hexyl ketone | (+)-2-Octanol | 17 |
| 35 | Acetophenone | (−)-1-Phenylethanol | 11 |
| Comparative Example 3 | " | " | 1 |

EXAMPLES 36 TO 42

The procedures in Example 31 were repeated except that 1-substituted 2-triazol-1-yl-4,4-dimethyl-1-penten-3-one having various substituents were used respectively in place of acetophenone used in Example 31. The results obtained are shown in Table 6.

EXAMPLE 43

The procedures in Example 31 were repeated except that 1-(2,4-dichlorophenyl)-2-triazol-1-yl-4,4-dimethyl-1-penten-3-one was used in place of acetophenone and (−)-1-(3-hydroxyphenyl)ethylamine was used in place of (+)-(2-hydroxyphenyl)ethylamine. The results obtained are shown in Table 6.

COMPARATIVE EXAMPLES 4 AND 5

The procedures in Example 43 were repeated except that (−)-1(4-hydroxyphenyl)ethylamine and (+)-α-phenylethylamine were used respectively in place of (−)-1(3-hydroxyphenyl)ethylamine used in Example 43. The results obtained are shown in Table 6.

TABLE 6

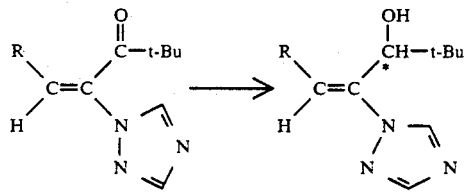

| | | Substrate (E-form/Z-form) | Boron hydride compound | Product E-form/Z-form | Optical* rotation | Optical* yield (%) |
|---|---|---|---|---|---|---|
| Example | R | | | | | |
| 36 | phenyl | 95/5 | $BH_3 \cdot SMe_2$ | 92.2/7.8 | (−) | 59 |
| 37 | 4-Cl-phenyl | 100/0 | $BH_3 \cdot THF$ | 99.3/0.7 | (+) | 77** |
| 38 | 3-Br-phenyl | 88.1/11.9 | $BH_3 \cdot SMe_2$ | 85.9/14.1 | (+) | 50 |
| 39 | 4-F-phenyl | 99.9/0.1 | " | 97.2/2.8 | (+) | 50 |

TABLE 6-continued $$R\underset{H}{\overset{R}{C}}=C\underset{N\diagdown N}{\overset{\overset{O}{\parallel}{C}-t-Bu}{N}} \longrightarrow R\underset{H}{\overset{R}{C}}=C\underset{N\diagdown N}{\overset{\overset{OH}{|}{CH}-t-Bu}{\overset{*}{N}}}$$

| | | | Product | | |
|---|---|---|---|---|---|
| | Substrate | Boron | | | |
| | (E-form/ | hydride | E-form/ | Optical* | Optical* |
| R | Z-form) | compound | Z-form | rotation | yield (%) |
| 40  CF$_3$—⬡— | 99.9/0.1 | " | 97.9/2.1 | (−) | 38 |
| 41  ⬡H— | 100/0 | " | 99.9/0.1 | (−) | 58 |
| 42  Cl—⬡—Cl | 99.8/0.2 | BH$_3$.THF | 99.0/1.0 | (+) | 73** |
| 43  Cl—⬡—Cl | 99.8/0.2 | BH$_3$.SMe$_2$ | 99.6/0.4 | (+) | 16 |
| Comparative Example | | | | | |
| 4 | " | " | BH$_3$.THF | 97.4/2.6 | (+) | 4 |
| 5 | " | " | " | 97.5/2.5 | (+) | 8 |

Note:
*E-form alcohol
**3.5 Equivalents of BH$_3$.THF was used relative to the ligand.

What is claimed is:

1. An optically active hydroxybenzylamine derivative represented by the formula (I)

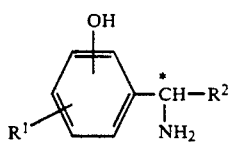  (I)

wherein $R^1$ denotes a hydrogen atom, lower alkyl group or lower alkoxy group; $R^2$ denotes a lower alkyl group; * signifies an asymmetric carbon atom; and the hydroxyl group is located on the phenyl at the ortho-or meta-position relative to the substituent having the asymmetric carbon atom.

2. The derivative according to claim 1, wherein the hydroxyl group is located on the phenyl at the ortho-position relative to the substituent having the asymmetric carbon atom.

3. The derivative according to claim 3, wherein $R^1$ is a lower alkoxy group.

4. The derivative according to claim 3, wherein the lower alkoxy group is substituted at the meta-position relative to the substituent having the asymmetric carbon atom.

5. The derivative according to claim 2, wherein $R^1$ is a hydrogen atom or lower alkyl group.

6. The derivative according to claim 1, wherein the hydroxyl group is located on the phenyl at the meta-position relative to the substituent having the asymmetric carbon atom.

7. A process for producing an optically active hydroxylbenzylamine derivative represented by the formula (I)

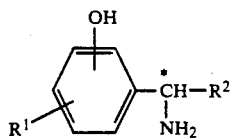  (I)

wherein $R^1$ denotes a hydrogen atom, lower alkyl group or lower alkoxy group; $R^2$ denotes a lower alkyl group; * signifies an asymmetric carbon atom; and the hydroxyl group is located on the phenyl at the ortho-or meta-position relative to the substituent having the asymmetric carbon atom, which comprises subjecting an optically active amine represented by the formula (IX)

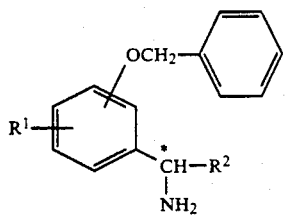 (IX)

wherein R¹ and R² are as defined above; * signifies an asymmetric carbon atom; and the benzyloxy group is located on the phenyl at the ortho- or meta-position relative to the substituent having the asymmetric carbon atom, or its acid salts thereof to hydrogenolysis in the presence of a hydrogenation catalyst.

8. The process according to claim 7, wherein the hydroxyl group is located on the phenyl at the ortho-position relative to the substituent having the asymmetric carbon atom.

9. The process according to claim 8, wherein R¹ is a lower alkoxy group.

10. The process according to claim 9, wherein the lower alkoxy group is located on the phenyl at the meta-position relative to the substituent having the asymmetric carbon atom.

11. The process according to claim 8, wherein R¹ is a hydrogen atom or lower alkyl group.

12. The process according to claim 7, wherein the hydroxyl group is located on the phenyl at the meta-position relative to the substituent having the asymmetric carbon atom.

* * * * *